US008391939B2

(12) United States Patent
Herrmann

(10) Patent No.: US 8,391,939 B2
(45) Date of Patent: Mar. 5, 2013

(54) METERING GLUCOSE LEVEL IN PULSING BLOOD

(75) Inventor: Vera Herrmann, Luebeck (DE)

(73) Assignee: Nirlus Engineering AG, Luebeck (DE)

( * ) Notice: Subject to any disclaimer, the term of this patent is extended or adjusted under 35 U.S.C. 154(b) by 678 days.

(21) Appl. No.: 12/376,187

(22) PCT Filed: Jul. 18, 2007

(86) PCT No.: PCT/EP2007/006362
§ 371 (c)(1),
(2), (4) Date: Nov. 25, 2009

(87) PCT Pub. No.: WO2008/014890
PCT Pub. Date: Feb. 7, 2008

(65) Prior Publication Data
US 2010/0298673 A1    Nov. 25, 2010

(30) Foreign Application Priority Data

Aug. 4, 2006  (DE) .......................... 10 2006 036 920

(51) Int. Cl.
*A61B 5/00* (2006.01)
*G01N 33/48* (2006.01)
(52) U.S. Cl. ........... 600/316; 600/310; 600/322; 356/39
(58) Field of Classification Search .................. 600/316, 600/310, 322, 476; 356/39, 301
See application file for complete search history.

(56) References Cited

U.S. PATENT DOCUMENTS

| 5,009,230 A | 4/1991 | Hutchinson ................... 128/633 |
| 5,222,496 A | 6/1993 | Clarke et al. .................. 128/633 |
| 5,553,613 A | 9/1996 | Parker ........................... 128/633 |
| 6,377,828 B1 * | 4/2002 | Chaiken et al. ................ 600/316 |
| 6,484,044 B1 | 11/2002 | Lilienfeld-Toal ............. 600/316 |
| 2004/0127779 A1 | 7/2004 | Steuer et al. ................... 600/335 |
| 2006/0009727 A1 | 1/2006 | O'Mahony et al. .......... 604/4.01 |
| 2006/0058595 A1 | 3/2006 | Herrmann ...................... 600/322 |

FOREIGN PATENT DOCUMENTS

WO    WO 9819592    5/1998

* cited by examiner

*Primary Examiner* — Rochelle-Ann J Blackman
(74) *Attorney, Agent, or Firm* — Andrew Wilford

(57) ABSTRACT

Method for the continuous measurement of the glucose concentration in blood undergoing pulsational flow, with the steps:—determination of a value for the glucose concentration for a first measurement cycle, and—repetition of the determination of this value in subsequent measurement cycles, where there is multiple detection, within each measurement cycle, of the transmittance and/or scattering power of the blood for at least two incident NIR wavelengths, calculation of an indicator value depending on the blood glucose concentration, and ascertaining the blood glucose concentration by comparing the indicator value with a previously determined calibration table, determination of the blood temperature during the detection of the transmittance and/or scattering power,—continuous measurement of the pulse duration of the pulsational blood flow, where the duration of the measurement cycle is arranged to keep in step as integral multiple of the pulse duration, where the first of the at least two NIR wavelengths is selected from the wavelength range 1560-1630 nm, and the second of the at least two NIR wavelengths is selected from the wavelength range 790-815 nm, and the ratio of the transmittance and/or scattering power of the at least two wavelengths is calculated, this ratio serving in relation to the blood temperature as indicator value for reading off the blood glucose concentration from the calibration table.

10 Claims, 1 Drawing Sheet

METERING GLUCOSE LEVEL IN PULSING BLOOD

CROSS REFERENCE TO RELATED APPLICATIONS

This application is the US national stage of PCT application PCT/EP2007/006362, filed 18 Jul. 2007, published 7 Feb. 2008 as WO2008/014890, and claiming the priority of German patent application 102006036920.3 itself filed 4 Aug. 2006.

FIELD OF THE INVENTION

The invention relates to a method for contact-free blood-sugar metering by means of NIR (near infrared) spectrometry in flowing, pulsing blood, which in particular is first removed from a living organism and returned again after a treatment, e.g. dialysis. The invention also relates to an apparatus that as an additional or integral component of a dialysis apparatus is suitable for monitoring the blood sugar content. Furthermore, the is invention is applicable in the noninvasive in vivo blood-sugar level monitoring.

BACKGROUND OF THE INVENTION

The determination of the blood-sugar level without direct contact with the blood, in particular without a special withdrawal of blood for this purpose, has been the subject of intensive medical research and development for more than two decades. The main objective thereby is the provision of a compact portable measuring apparatus for diabetics, which ideally can quickly provide reliable sugar values at the most through skin contact and without injuring the skin. Despite considerable efforts by numerous researchers, which have produced a large number of interesting approaches to a solution, to date no satisfactory measuring apparatus of this type has reached market readiness.

The prior art, which at this point can be cited only in extracts, deals both with in vivo as well as in vitro measurement, where very often a transfer is made directly from experimental in vitro results to the in vivo case. However, a transfer of this kind is in principle untenable, since it does not take into consideration at all or only incompletely the considerable complications of the interactions of all blood constituents and the solid tissue with light.

Thus, for example, in reality the proposal sometimes made of the analysis of the NIR light scattered back from the living body is a problem per se in a class of its own, in which the informative value of the scattered light is firstly questionable. Since scattered photons follow a nonlinear path, influenced by multiple scattering, back to the surface of the body, it must be decided at the detector which portion of light has run through a blood vessel at all and thus has information about the blood-sugar level. Such a source localization by itself is technically complex and is described, e.g. in DE 103 11 408 [U.S. Pat. No. 7,251,518].

Some sources therefore dedicate themselves primarily to the question of the physical measured variable that is to be used for glucose metering. The metrological details that an in vivo measurement would actually require are, in contrast, simply assumed to be technically soluble.

Thus, for example, U.S. Pat. No. 5,009,230 proposes measuring the change of the polarization of linearly polarized IR light when passing through perfused tissue, in concrete terms the rotation of the polarization plane by glucose molecules. The measurable light intensity behind a polarization filter is used to determine the concentration. It is thereby considered important for the sensitivity to change periodically between polarization directions perpendicular to one another.

It is known from U.S. Pat. No. 5,222,496 that the intensity of transmitted or reflected NIR light is to be placed in proportion to one another for several wavelengths in order to measure the glucose level. In particular light around 1600 nm wavelength is used, which is absorbed particularly well by glucose due to molecular fluctuations. In contrast, for this wavelength range water has a local absorption minimum. In order to compensate for the signals of other blood constituents, as well as the influence of the is surrounding tissue or, for example, the pigmentation of the skin with the in vivo measurement, U.S. Pat. No. 5,222,496 suggests the additional use of at least one further wavelength in the vicinity of the first, which in turn is not to be absorbed by glucose. Particular importance is attached to the slight difference of the wavelengths—less than 300 nm, preferably 60 nm—in order to ensure the same type of scatter behavior.

However, both sources are not concerned at all, for example, with the movement of the blood in the living organism. Also the knowledge of the temperature of the blood, doubtlessly necessary for spectrometric analysis, is referred to only briefly in U.S. Pat. No. 5,009,230, but by no means dealt with.

It is presumably due to the obviously immense complexity of the measurement task that indirect methods for determining blood sugar are also repeatedly proposed. Photoacoustic measurement is cited by way of example here, in which living tissue is irradiated with different wavelengths in order to detect the thermal expansion during the absorption of the radiation in the form of detectable ultrasonic waves on the skin's surface, see, e.g. U.S. Pat. No. 6,484,044. The wavelengths are also selected hereby according to the known absorption maximums of glucose, and likewise differential measurements are carried out for the purpose of signal isolation.

However, the fundamental problem of complexity is thus by no means circumvented, let alone solved. As already with the backscatter of photons, here too the information content of the sound signals is uncertain, their precise source localization is unclear and their formation certainly influenced by numerous highly individual and possibly even changeable tissue parameters. The photoacoustic method is ultimately a highly empirical method, which evidently has difficulty finding a standard calibration for broad applicability.

In conclusion, the GlucoWatch® method should be referenced as prior art, which is the only one on the market so far with FDA approval. GlucoWatch® indeed does not require a blood sample for analysis, but is attached to the skin of the wearer such that it can take up fluid through the skin. Users have frequently reported skin irritations and, furthermore, even the manufacturer advises against using GlucoWatch® as the only means of judging the correct insulin dosage.

The applicant believes a method for noninvasive blood glucose measurement will generally not be able to do without empirical data interpretation. However, this should remain limited in the interest of the most universal possible applicability of a system of this type to partial areas of the method that can be monitored well.

The following objects must be attained in order to create a noninvasive system:
1. Blood-sugar metering in flowing, pulsing blood (in vitro) recording empirical, largely universal calibration curves,
2. Transferring the method from the in vitro structure to preferably large blood vessels (e.g. aorta) by a. Source localization, elimination of signals is without information,
b. Compensation for tissue and skin influences on the remaining signal,
c. In situ temperature determination in the blood vessel and interstitial tissue for application of the calibration curves.

Considerable preliminary work has already been published by the applicant re points 2a and 2b in DE 103 11 408. The object 2c is the subject matter of future work and will be submitted in a separate application in due course. The present application deals solely with object 1. U.S. Pat. No. 5,222,496 is deemed to be the closest pertinent prior art in this case.

The in vitro determination of the blood-glucose level is of interest per se for integration into dialysis equipment.
Studies in the US show the importance of the continuous monitoring above all in the case of dialysis patients with diabetes. In the absence of suitable apparatuses, cases of death have already been recorded.

OBJECT OF THE INVENTION

The object of the invention is therefore to provide a method and an apparatus for the contact-free measurement of blood-glucose level in flowing pulsing blood.

SUMMARY OF THE INVENTION

The object is attained through the method comprising the steps of:
determining the blood temperature during the detection of the transmission and/or scattering power, continuously measuring the pulse duration of the pulsing blood flow with a measuring cycle whose duration is set to keep in step as integral multiple of the pulse duration. Then the first of the at least two NIR wavelengths is selected from the wavelength range 1560-1630 nm, and the second of the at least two NIR wavelengths being selected from the wavelength range 790-815 nm. Finally, the ratio of the transmission and/or scattering power of the at least two wavelengths is calculated with this ratio serving in relation to the blood temperature as an indicator value for reading off the blood-glucose level from the calibration table.

The invention is based on the discovery that the scatter behavior of the flowing pulsing blood for NIR light (measurement light) has a dominant influence on transmitted and/or scattered measurement light intensities.

The light scattering in a blood sample at rest is already very marked by the blood substances present therein (such as lipid, alcohol, etc.), but also by the number and shape of the scatter particles present in the blood plasma—in particular red and white blood corpuscles that do not have a spherical form. Even in blood at rest these particles move with respect to one another, rotate their relative position and cause a continuous change in the anisotropic scattering power. The intrinsic movement of the scatter particles is related to the temperature of the blood sample. Furthermore, the NIR absorptive capacity of water is also dependent on the temperature.

It is therefore a first feature of the invention to determine the blood temperature through a separate measurement, where at least a precision of 0.5° C., preferably even 0.1° C. or better must be achieved.

In order to prevent the intensity of the transmitted or back-scattered measurement light from being susceptible to particle-based scattering, it was found that a statistical averaging of the measured values must be carried out via a plurality of successive time windows. The time windows should thereby preferably each be a few milliseconds, but no more than 100 ms long, and in their entirety (comprising a sequence of nonoverlapping time windows, referred to below as a measurement cycle) cover a time period of at least one second, preferably 2-3 seconds. Thus at least 10, but preferably 200 or more, discrete time windows are available for the evaluation.

Within each of the time windows, furthermore, at least 10,000 discrete measured values are to be recorded, preferably as many as 30,000. The measured values within the time window therefore cover intensity fluctuations on the microsecond scale. This scale is not relevant for the spontaneous movement of the blood, i.e. the blood is quasi static. It is used instead to separate the light signals (see below).

According to the invention the at least 10,000 measured values recorded per time window are registered by a process control computer (e.g. PC with data acquisition card) and stored in an array. The measured values of the following time window are recorded in the same number and added to the same array. The stored measured values thus grow in a cumulative manner with each further time window until the measurement cycle ends (at least 10 time windows, minimum measurement duration 1 second). Subsequently, the accumulated measured value array can be divided is by the number of contributing time windows for normalization. However, normalization is not obligatory, since measurement ratios are used in the further process.

For a blood sample at rest, this procedure is sufficient to eliminate the influences of the movement of scattering particles in the blood by averaging. For the measured values recorded in an individual time window an ensemble average is thus carried out over all the movement conditions of the blood. Nevertheless, the extent of the particle movement in the blood plasma is determining for the effective average scattering strength of the sample. The scattering strength variability is leveled by the ensemble average, but not absolutely determined. For this reason alone, the temperature measurement is also necessary.

When the blood flows in pulses manner during the measurement, further movement conditions of the blood take place, which essentially are periodically repeated with the pulse frequency. The blood is in particular subjected to pressure fluctuations and will have additional turbulences and differences in density. Therefore according to the invention the ensemble average—and thus the length of the measurement cycle—is extended over at least one complete pulse duration. In the case of a healthy adult when awake, the pulse frequency is approximately 1 Hz, so that this is easily possible within the above-referenced specification of the measurement cycle of 2 to 3 seconds. According to the invention the measurement cycle is adjusted as precisely as possible to an integral multiple of the pulse duration in order to take into account each recurring movement condition of the blood with the same weight in the ensemble average.

The pulse frequency on the one hand can thereby be recorded separately by sensors and transmitted to the process control computer so that it continuously calculates anew the number and length of the individual time windows and actuates the data acquisition unit accordingly. However, it is generally even possible to conclude the pulse frequency directly from the recorded measured values. To this end, the ensemble average outlined above is first carried out with the specification of a hypothetical pulse frequency and then optimized with the variation of the pulse frequency as fit parameter.

For optimization, for example, the integrated measurement signal can serve as characteristic value over the individual time window after ensemble average (the at least 10,000 cumulated measured values), which is a gauge for the overall scattering strength of the blood. Although the latter is dependent on temperature, over the short time period of successive measurement cycles (several times 2-3 seconds), the temperature can be assumed to be virtually constant. If the ensemble of blood movement conditions is selected unfavorably with respect to the pulse duration, the characteristic value will show clear variations between consecutive measurements. The optimality criterion is here the minimization of these variations.

Certainly other measurement and/or calculation methods for the pulse duration can be found and used. According to the invention it is important here to take into account the pulse duration in the establishment of the time window and the measurement cycle for the statistical evaluation. Furthermore, it can be advantageous to work with fixedly selected time windows of a maximum of 100 ms, so that it is not possible here to scan the entire pulse exactly with an entire number of time windows. In this case, the introduction of a measurement dead time is recommended, generally less than the fixed time window in order to establish the desired synchronicity with the pulse. Measurement dead time means that measured values of the light detectors are not considered or are not generated at all during this period. The measurement dead time can as described above also be dynamically optimized.

Preferably the measurement cycle is extended over a plurality of pulses. However, this plurality is typically a small number (<10), since a measured value must be available within a few seconds. This is particularly important for an in vivo system, in which the user has to carry out the measurement himself. Longer measurement durations are a reason for movement artifacts.

For the spectrometric determination of the blood-glucose level in part U.S. Pat. No. 5,222,496 is now followed, in that an NIR wavelength from the range 1560-1630, preferably 1600 nm is irradiated into the blood. Basically transmission and/or scattering strength of the blood can be measured for the selected wavelengths and used as an indicator for the blood-glucose level.

With in vitro measurement, preferably the transmission of irradiated light is recorded in order to measure the extinction coefficient (also: optical density). This is defined as the negative decadic logarithm of the ratio of the transmitted to the irradiated light intensity. It is calculated from the at least 10,000 measured values of the determined time window after the ensemble average.

In the determination of the extinction coefficient it should be noted that the IR light detector can also record undesired light portions that falsify the data. Although it is possible to use different detectors with different chromatic sensitivity, these too register extraneous light in their respective sensitive wavelength range. Therefore the irradiated light is preferably amplitude-modulated with a modulation frequency of at least 1 MHz, particularly preferably 3-4 MHz. This amplitude modulation in the at least 10,000 measured values within the time window lasting a maximum of 100 ms is in principle resolvable and permits the spectrum analysis of the data in the time window. A spectral representation of the measured values of the time window after the ensemble average is calculated preferably by means of fast Fourier transformation. In the further evaluation then only Fourier components from the range of the modulation frequency are included. This way in the simplest case the Fourier components can be determined for modulation frequency alone optionally through interpolation and assumed as a gauge for the transmitted intensity. However, it has proven to be advantageous instead to use a numerical integral over the Fourier spectrum in the frequency range, wherein values are added in a window having the width $2 \Delta f$. The modulation frequency thereby lies centrally in the integration window. The value $\Delta f$ should be selected to be as small as possible but sufficiently large to compensate for fluctuations between consecutive measurements (at intervals of a few seconds) between which the physical variable to be measured cannot have changed substantially. This is therefore a fit parameter that is automatically varies during the measurement and can be adjusted. Preferably it is at some time stored as a constant in the evaluation unit and used again for later measurements. Of course, it can be checked from time to time and readjusted.

Unmodulated extraneous light is virtually eliminated after the above. The irradiated intensity, however, scales with the laser power and is known. The extinction coefficient can thus be given as defined above The extinction coefficient E, as described above, depends on the movement conditions of the blood, but also simply on the composition of the blood particles, in particular with respect to type and number, that is, on the hematocrit values, which can differ substantially among different people. Furthermore, the fat level in the blood plays a role, which can vary even hour by hour in the same person.

For compensation, therefore, at the same time a second NIR wavelength is irradiated, the transmission of which depends only on hematocrit values and fat content, but not on other factors such as blood sugar or, e.g. the oxygen saturation of the blood. For this the "isobestic" wavelength lends itself at approximately 808 nm in particular, for which the absorptive capacity of oxyhemoglobin and deoxyhemoglobin is known as identical. It lies at the same time in the extended absorption minimum of water. Here the approach according to the invention already differs significantly from the teaching of U.S. Pat. No. 5,222,496.

Basically, variations of the cited wavelengths are possible, i.e. also values in the vicinity of 808 nm (probably in the range of 790-815 nm) can be considered. Since the light preferably is irradiated from laser diodes, it can here be considered as a technically very advantageous embodiment instead of two lasers to use only a single one with a frequency doubler and beam splitter. This can be used to place the irradiated intensities of the different wavelengths in a fixed ratio to one another in principle independent of pump capacity and laser control.

For the isobestic wavelength, the extinction coefficient EISO is measured. The ratio R=E/EISO is determined in the process control computer and the blood-sugar level can be read off based on the calibration function K (R, T) available as a table in the computer. The value T is thus the blood temperature to be measured at the same time, which in the simplest case is to be detected in the in vitro measurement by means of a temperature sensor. It is not necessary to bring the sensor into direct contact with the blood, but it can be installed on the outside on a measuring cell. Furthermore, there is also the possibility of detecting the temperature via the infrared irradiation emitted by the blood, when the NIR laser sources are temporarily switched off (e.g. during the above-referenced measurement dead time, at least one IR detector is available anyway).

The calibration table K (R, T) is to be determined on the one hand in that NIR measurement values are determined with blood glucose data from other measurement processes, for example, by means of measurement strips.

BRIEF DESCRIPTION OF THE DRAWING

A concrete illustrated embodiment is given below for a is system for in vitro blood-sugar metering and the results of a few exemplary measurements are presented. This is supported by the following figures.

DETAILED DESCRIPTION

Figure 1:
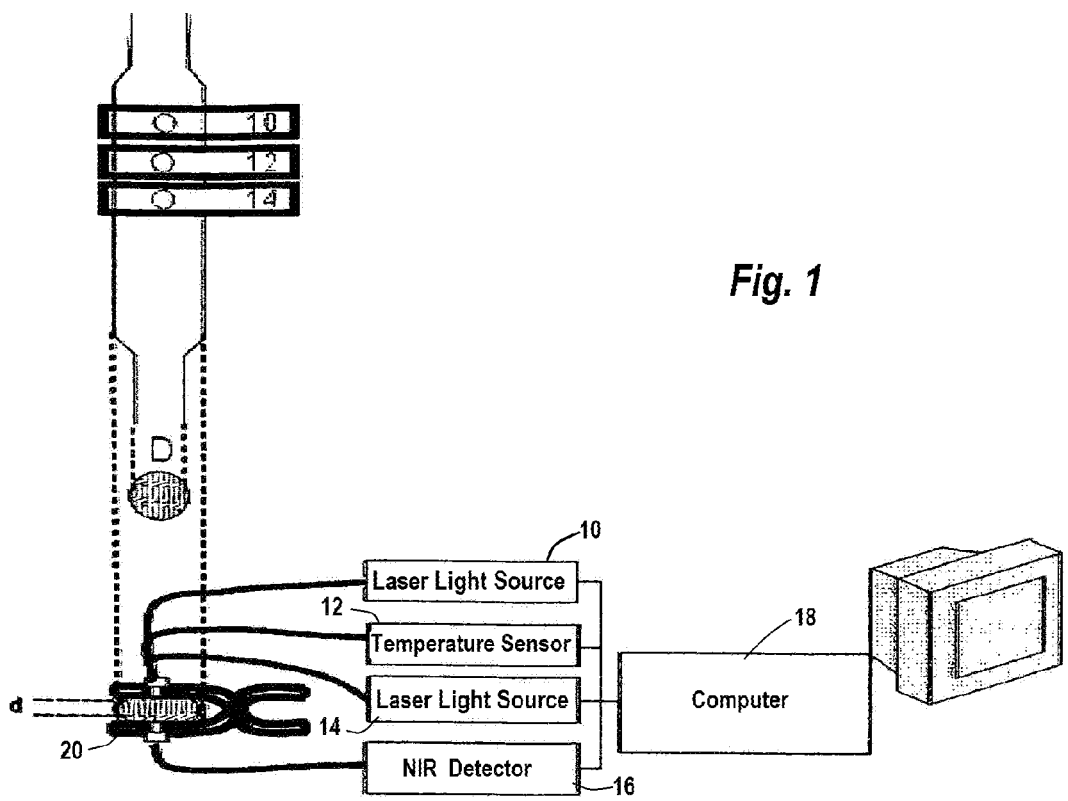
FIG. 1 shows a structural sketch of the apparatus for carrying out the method described here.

FIG. 1 shows in the upper area of the image the side view of a measuring cell, where on one side (in this case, that turned toward the viewer) two laser light sources 10 and 14 as well as a temperature sensor 12 are arranged. The laser light sources 10 and 14 are preferably the exit ends of optical fibers, but can also be laser diodes that have an electric supply in situ. In the laboratory experiment shown below, tunable laser sources of the type High Performance Tunable Laser TSL-510 are used, which, however, for reasons of cost alone is not intended to be a preferred embodiment of the invention. The irradiation power in the apparatus described here should preferably be 10 mW.

The temperature sensor 12 measures the outside temperature of the cell. This can easily be used by one-time calibration to determine the blood temperature. However, it should be ensured that the measuring cell is insulated very well with the temperature sensor 12 from temperature fluctuations. Otherwise, even the opening of a window could lead to incorrect measurements.

A measuring cell that, for example, is integrated into the feed lines of a dialysis apparatus should comprise a material permeable to NIR light (e.g. quartz glass, CIR-Chalcogenide IR-Glass) and typically has in the area of the connections to the feed lines a circular cross section of D=4.2-4.5 mm diameter (cf. FIG. 1) In the trans-illumination zone the diameter in the irradiation direction must be reduced to approximately d=2. FIG. 1 below shows a cross-sectional representation, where a clamp 20 is used to hold the flattened measuring cell. Likewise shown are the laser sources 10 and 14 and the temperature sensor 12 on the one side of the measuring cell. On the opposite side of the measuring cell at least one NIR detector 16 is arranged that measures the transmitted radiation. Concretely, an NFI-2053-FC-M 10 MHz InGaAs photoreceiver was used. An NIR laser is preferred with beam splitter and frequency doubling medium which at the same time emits NIR light at 1560-1630 nm wavelength as well as NIR light with half the wavelength to show the at least two NIR light sources.

FIG. 1 finally also shows a computer-supported data acquisition and evaluation unit 18 as well as a display of the determined values for the blood-glucose level. Here for example the high-speed data acquisition card WA1-100-110 from Acquitec with a scanning rate of 20 MHz and a resolution of 12 Bit, as well as an AcquiFlex oscilloscope, waveform editor and logic analyzer software are recommended. The apparatus operates as described above and now permits the continuous monitoring of the blood.

Figure 2:
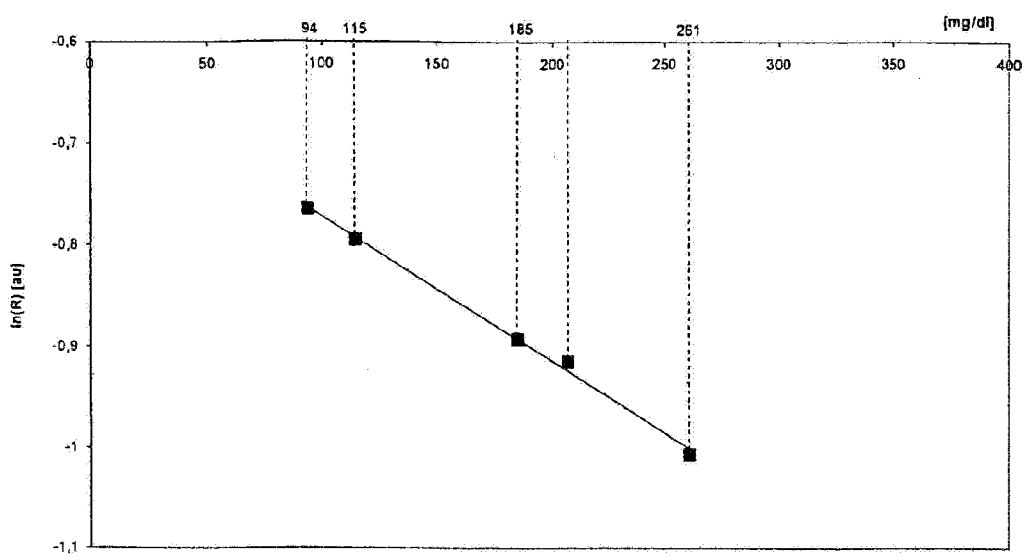
FIG. 2 compares the spectrometrically measured blood sugar values with those of a simultaneous measurement by means of blood sugar test strip according to the prior art.

FIG. 2 illustrates based on some exemplary measurements of human blood that the calibration necessary for using the apparatus and the method according to the invention can be determined. To this end first reference values (e.g. with the commercial Accu-Chek® blood-sugar metering apparatus, but better with much more precise analysis methods) is determined on test subjects. On the abscissa the "true" blood sugar values are entered in units mg/dl and the ordinate shows the logarithm of the intensity ratio R, as it is determined with the method described above on blood samples taken by the doctor from the same test subjects. Evidently the "true" values—although they can also still exhibit errors themselves—are arranged approximately along a trend line. This trend line can be used as a calibration curve for converting the spectrometric values—if the blood temperature is known.

FIG. 2 shows only preliminary initial results. The calibration curves are to be determined for a plurality of blood temperatures and of course with a much greater number of blood samples.

The invention claimed is:

1. A method for the continuous measurement of glucose level in blood undergoing pulsing flow, the method comprising the steps of:
    determining a value for the glucose level in succeeding and nonoverlapping time windows of the same length of a first measurement cycle;
    repeating the determination of this value in subsequent measurement cycles with the same number of nonoverlapping time windows of the same length such that there is multiple detection within each measurement cycle of the transmission or scattering power of the blood for at least two incident NIR wavelengths, calculation of an indicator value dependent on the blood-glucose level and ascertaining the blood-glucose level by comparing the indicator value with a previously determined calibration table;
    determining ensemble averages for all the time windows of each measurement cycle;
    determining the blood temperature during the detection of the transmission and/or scattering power,
    continuously measuring the pulse duration of the pulsing blood flow, the duration of the measurement cycle being set to keep in step as integral multiple of the pulse duration,
    selecting the first of the two NIR wavelengths from the wavelength range 1560-1630 nm, and the second of the NIR wavelengths from the wavelength range 790-815 nm, and
    using the ratio of the transmission or scattering power of the two wavelengths relative to the blood temperature as an indicator value for reading off the blood-glucose level from the calibration table.

2. The method according to claim 1 wherein the at least two NIR wavelengths are irradiated in an amplitude-modulated manner with modulation frequencies above 1 MHZ.

3. The method according to claim 1 wherein each time window comprises less than 100 milliseconds.

4. The method according to claim 1 wherein the number of the measured values for transmission and/or scattering power of the blood in each time window is at least 10,000.

5. The method according to claim 1 wherein the average measured values in the determined time window are subjected to a Fourier transformation in the frequency range.

6. The method according to claim 5,
    further comprising the step of:
    evaluating the Fourier components of the average measured values for modulation frequency of the amplitude modulation of the irradiated NIR wavelengths as a gauge for the transmission or scattering power of the blood.

7. The method according to claim 6 wherein an integral in the frequency range over the Fourier components of the average measured values at an interval around the modulation frequency of the amplitude modulation of the irradiated NIR wavelengths is evaluated as a gauge of the transmission or scattering power of the blood.

8. An apparatus for carrying out the method according to claim 1 wherein the blood is taken from a living organism in a circulation, measured and returned, the apparatus further comprising:
- a measuring cell embodied for the continuous inflow and outflow of blood with a trans-illumination zone embodied in a flattened manner,
- at least two NIR light sources arranged on a flat side of the measuring cell for trans-illuminating the measuring cell in the direction toward the opposite flat side,
- at least one NIR detector arranged on the flat side, which lies opposite that with the NIR light sources, and
- means for measuring the blood temperature at least in the trans-illumination area of the measuring cell.

9. The apparatus according to claim 8, further comprising
- an NIR laser with beam splitter and frequency doubling medium, which at the same time emits NIR light with 1560-1630 nm wavelength as well as NIR light with half the wavelength to show the at least two NIR light sources.

10. A method for the continuous measurement of glucose level in blood undergoing pulsing flow, the method comprising the steps:
- determining a value for the glucose level for a first measurement cycle;
- repeating the determination of this value in subsequent measurement cycles such that there is multiple detection within each measurement cycle of the transmission or scattering power of the blood for at least two incident NIR wavelengths, calculation of an indicator value dependent on the blood-glucose level and ascertaining the blood-glucose level by comparing the indicator value with a previously determined calibration table;
- determining the blood temperature during the detection of the transmission and/or scattering power,
- continuously measuring the pulse duration of the pulsing blood flow, the duration of the measurement cycle being set to keep in step as integral multiple of the pulse duration,
- selecting the first of the at least two NIR wavelengths from the wavelength range 1560-1630 nm, and the second of the at least two NIR wavelengths from the wavelength range 790-815 nm,
- using the ratio of the transmission or scattering power of the at least two wavelengths being calculated with this ratio relative to the blood temperature as an indicator value for reading off the blood-glucose level from the calibration table, and
- synchronously adjusting the duration of the measurement cycle to the continuously recorded pulse duration of the blood using a variable number of time windows with fixed duration and adding a variable measurement dead time, the number of the time windows and the measurement dead time being calculated synchronously.

* * * * *